US008053490B2

(12) United States Patent
Jia et al.

(10) Patent No.: US 8,053,490 B2
(45) Date of Patent: Nov. 8, 2011

(54) PRE-TREATED ACID-REACTIVE FILLERS AND THEIR USE IN DENTAL APPLICATIONS

(75) Inventors: Weitao Jia, Wallingford, CT (US); Shuhua Jin, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 115 days.

(21) Appl. No.: 12/467,448

(22) Filed: May 18, 2009

(65) Prior Publication Data

US 2010/0292360 A1    Nov. 18, 2010

(51) Int. Cl.
*C08F 2/50* (2006.01)
*A61K 6/00* (2006.01)
*A61K 6/08* (2006.01)
*A61K 6/083* (2006.01)
*C08J 3/28* (2006.01)

(52) U.S. Cl. ........ 523/113; 523/109; 523/112; 523/114; 523/115; 523/116; 523/117; 523/118; 523/120; 522/71; 522/74; 522/79; 522/113; 522/114; 522/119; 522/120; 522/121; 522/908; 524/1; 524/3; 524/5; 524/847; 524/858; 524/859; 524/878; 524/881

(58) Field of Classification Search .................... 522/79, 522/71, 74, 77, 113, 114, 119, 120, 121, 522/908; 524/1, 3, 5, 8, 847, 585, 859, 878, 524/881; 523/105, 109, 112, 113, 114, 115, 523/116, 117, 118, 120

See application file for complete search history.

(56) References Cited

U.S. PATENT DOCUMENTS

| | | | |
|---|---|---|---|
| 4,306,913 A | 12/1981 | Mabie et al. | |
| 4,503,169 A | 3/1985 | Randklev | |
| 4,530,992 A * | 7/1985 | Jones | 528/232 |
| 4,544,359 A | 10/1985 | Waknine | |
| 4,547,531 A | 10/1985 | Waknine | |
| 4,593,054 A | 6/1986 | Asmussen et al. | |
| 4,599,373 A * | 7/1986 | Jones | 523/116 |
| 4,673,725 A * | 6/1987 | Jones | 528/266 |
| 4,719,149 A | 1/1988 | Aasen et al. | |
| 4,739,032 A * | 4/1988 | Jones | 528/230 |
| 4,802,950 A | 2/1989 | Croll | |
| 4,880,660 A | 11/1989 | Aasen et al. | |
| 5,061,183 A | 10/1991 | Nicholson | |
| 5,063,257 A | 11/1991 | Akahane et al. | |
| 5,130,347 A | 7/1992 | Mitra | |
| 5,256,065 A | 10/1993 | Nicholson | |
| 5,264,513 A | 11/1993 | Ikemura et al. | |
| 5,276,068 A | 1/1994 | Waknine | |
| 5,444,104 A | 8/1995 | Waknine | |
| 5,525,648 A | 6/1996 | Aasen et al. | |
| 5,756,560 A | 5/1998 | Antonucci et al. | |
| 5,865,623 A | 2/1999 | Suh | |
| 5,883,153 A | 3/1999 | Roberts et al. | |
| 5,925,690 A | 7/1999 | Fuchigami et al. | |
| 5,954,996 A | 9/1999 | Discko, Jr. | |
| 5,969,000 A | 10/1999 | Yang et al. | |
| 6,004,390 A | 12/1999 | Pflug et al. | |
| 6,013,694 A | 1/2000 | Jia et al. | |
| 6,071,983 A | 6/2000 | Yamamoto et al. | |
| 6,126,922 A | 10/2000 | Rozzi et al. | |
| 6,127,451 A | 10/2000 | Qian | |
| 6,147,137 A | 11/2000 | Jia | |
| 6,214,101 B1 | 4/2001 | Nakaseko | |
| 6,217,644 B1 | 4/2001 | Matsunae et al. | |
| 6,270,562 B1 | 8/2001 | Jia | |
| 6,291,548 B1 | 9/2001 | Akahane et al. | |
| 6,312,667 B1 | 11/2001 | Trom et al. | |
| 6,355,704 B1 | 3/2002 | Nakatsuka et al. | |
| 6,387,981 B1 | 5/2002 | Zhang et al. | |
| 6,403,676 B1 | 6/2002 | Jia et al. | |
| 6,417,246 B1 | 7/2002 | Jia et al. | |
| 6,437,019 B1 | 8/2002 | Rusin et al. | |
| 6,572,693 B1 | 6/2003 | Wu et al. | |
| 6,613,812 B2 | 9/2003 | Bui et al. | |
| 6,620,861 B1 | 9/2003 | Nakatuka et al. | |
| 6,653,365 B2 | 11/2003 | Jia | |
| 6,730,715 B2 | 5/2004 | Jia | |
| 6,759,449 B2 | 7/2004 | Kimura et al. | |
| 6,765,038 B2 | 7/2004 | Mitra | |
| 6,767,955 B2 | 7/2004 | Jia | |
| 6,815,470 B2 | 11/2004 | Ibaragi et al. | |
| 6,939,900 B2 | 9/2005 | Ario et al. | |

(Continued)

FOREIGN PATENT DOCUMENTS

DE        19906834 A1 *  8/1999

(Continued)

OTHER PUBLICATIONS

The International Searching Authority, International Search Report, PCT/US2007/004458, issued on Mar. 27, 2008, 4 pages.

(Continued)

Primary Examiner — Sanza McClendon
(74) Attorney, Agent, or Firm — Wood, Herron & Evans, LLP

(57) ABSTRACT

A dental filler and dental resin restorative composition containing the dental filler is provided. The dental filler is prepared by pre-treating an acid-reactive filler with a polymerizable monomer or oligomer pre-treatment chemical having at least one acid or acid-precursor functional group, at least one polymerizable unsaturated carbon-carbon bond, and a molecular weight of about 1,000 grams per mole or less.

22 Claims, No Drawings

U.S. PATENT DOCUMENTS

| | | |
|---|---|---|
| 7,090,722 B2 | 8/2006 | Budd et al. |
| 7,091,259 B2 | 8/2006 | Bui et al. |
| 7,361,216 B2 | 4/2008 | Kangas et al. |
| 7,700,667 B2 * | 4/2010 | Jia et al. ............ 523/115 |
| 2004/0054027 A1 | 3/2004 | Lyons et al. |
| 2004/0156795 A1 | 8/2004 | Nemoto et al. |
| 2004/0229973 A1 | 11/2004 | Sang et al. |
| 2004/0235981 A1 | 11/2004 | Qian |
| 2005/0014861 A1 | 1/2005 | Qian |
| 2005/0049326 A1 | 3/2005 | Park et al. |
| 2005/0192374 A1 | 9/2005 | Jia et al. |
| 2005/0277706 A1 | 12/2005 | Han et al. |
| 2006/0084717 A1 | 4/2006 | Cohen |
| 2006/0247329 A1 | 11/2006 | Moszner et al. |
| 2007/0197682 A1 | 8/2007 | Jia et al. |
| 2007/0197683 A1 | 8/2007 | Jia et al. |
| 2007/0299157 A1 | 12/2007 | Sang et al. |
| 2008/0242761 A1 | 10/2008 | Jia et al. |

FOREIGN PATENT DOCUMENTS

| | | |
|---|---|---|
| EP | 1767184 A1 * | 3/2007 |
| EP | 2163232 A1 * | 3/2010 |
| EP | 2163233 A1 * | 3/2010 |
| JP | 57075908 A | 5/1982 |
| JP | 58083605 A * | 5/1983 |
| JP | 06219918 A * | 8/1994 |
| JP | 2002087917 A * | 3/2002 |
| JP | 2004051554 A * | 2/2004 |

OTHER PUBLICATIONS

The International Searching Authority, Written Opinion of the International Searching Authority, PCT/US2007/004458, issued on Aug. 26, 2008, 7 pages.

Robert G. Craig, Restorative Dental Materials, 9th Edition, 1993, pp. 197-199, Mosby, St. Louis.

Robert G. Craig, Restorative Dental Materials, 9th Edition, 1993, pp. 68-69, Mosby, St. Louis.

European Patent Office, Search Report and Preliminary Opinion issued in corresponding European Patent Application No. EP-10250866 dated Sep. 16, 2010, 3 pp.

* cited by examiner

PRE-TREATED ACID-REACTIVE FILLERS AND THEIR USE IN DENTAL APPLICATIONS

FIELD OF INVENTION

The present invention relates generally to filler materials and methods of manufacture thereof and more specifically to filler materials for use in dental composite materials.

BACKGROUND OF INVENTION

Compositions useful for repairing damaged teeth in, situ are known in the art as direct filling materials, and include alloys and resin composites. Amalgam dental fillings are being increasingly replaced with dental composites that more closely match the color and appearance of the natural tooth. These composites generally contain an organic resin with a microparticle filler. Most systems incorporate a light- or UV-curable polymeric resin, such as a diglycidylmethacrylate of bisphenol. A (BIS-GMA), triethyleneglycol dimethacrylate (TEGDMA) or a urethane dimethacrylate (UDMA). The filler particles are typically barium silicate glass, quartz, or zirconium silicate, combined with small colloidal silica particles.

Increasingly, composite formulations have also included glass ionomers, which are known to release fluoride. Cariostatic properties are attributed to fluoride and thus, glass ionomer cements are associated with favorable cariostatic behavior. Another important aspect of glass ionomer cements is the strong clinical adhesion of such cements to tooth structure, thus providing highly retentive restorations.

One disadvantage associated with glass ionomer cement materials is they are generally supplied as a two-component system, with one part being in liquid form and the other in powder form. The liquid is typically a polyacrylic acid or its co-polymer in water. The powder part is commonly a fluoroaluminosilicate (FAS) glass, with an exemplary formula of

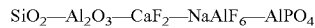

$SiO_2$—$Al_2O_3$—$CaF_2$—$NaAlF_6$—$AlPO_4$

Two-component packaging is generally necessary because a glass ionomer powder can readily react with polyacrylic acid or its co-polymer in the presence of water. As such, the glass ionomer powder is packaged separately from the polyacrylic acid, in order to have a shelf-life or storage life. Alternatively, a powder form of both the polyacrylic acid and the glass ionomer may be premixed and water added just prior to use. Some paste-paste versions of the glass ionomer cements have also been developed. In those cases, however, the glass ionomer powders are mixed with a non-reactive component to form one paste and the polyacrylic acid component comprises the other paste. In any event, the foregoing examples provide for two-component dental resin restorative compositions that are mixed just prior to use. The mixture will undergo self-hardening in the dark due to the ionic reaction between the acidic repeating units of the polyacrylic acid and cations leached from the glass.

One shortcoming of the conventional glass ionomer cements is that they can be technique sensitive. For example, their performance can be affected by the mixing ratio, as well as the manner of mixing. Additionally, they are quite brittle, as evidenced by their low flexural strength and tend to undergo fracture quite readily. Therefore, it would be desirable to attain a glass ionomer composition as a one-component dental resin restorative composition that does not require any premixing just prior to use. It would be desirable that this composition be light curable, mechanically strong, stable, and capable of releasing fluoride.

SUMMARY OF THE INVENTION

In one embodiment of the invention, a pre-treated dental filler is provided comprising a reaction product of an acid-reactive filler and a pre-treatment chemical. The pre-treatment chemical is a polymerizable monomer or oligomer comprising at least one acid or acid-precursor functional group, at least one polymerizable unsaturated carbon-carbon bond, and a molecular weight of about 1,000 grams per mole or less.

In another embodiment of the invention, a dental resin restorative composition is provided comprising a polymerizable resin, a pre-treated dental filler and a polymerization initiator. The pre-treated dental filler comprises a reaction product of an acid-reactive filler and a pre-treatment chemical. The pre-treatment chemical is a polymerizable monomer or oligomer comprising at least one acid or acid-precursor functional group, at least one polymerizable unsaturated carbon-carbon bond, and a molecular weight of about 1,000 grams per mole or less.

In another embodiment of the invention, a method of making a polymerizable dental composite is provided comprising forming a pre-treated dental filler and combining the pre-treated dental filler with a polymerizable resin and a polymerization initiator. The pre-treated dental filler comprises a reaction product of an acid-reactive filler and a pre-treatment chemical. The pre-treatment chemical is a polymerizable monomer or oligomer comprising at least one acid or acid-precursor functional group, at least one polymerizable unsaturated carbon-carbon bond, and a molecular weight of about 1,000 grams per mole or less.

DETAILED DESCRIPTION OF THE INVENTION

The present invention is directed to a filler material that can be used to form dental composites and restorations in accordance with known procedures. The resulting filler material can be used in dental composites and dental restorations including but not limited to fillings, orthodontic retainers, bridges, space maintainers, tooth replacement appliances, dentures, crowns, posts, jackets, inlays, onlays, facings, veneers, facets, implants, abutments, cements, bonding agents and splints, to provide optimal handling properties, good wear resistance and high strength.

The pre-treated dental filler according to the present invention is a reaction product of an acid-reactive filler and a pre-treatment chemical. The pre-treatment chemical is a polymerizable monomer or oligomer comprising at least one acid or acid-precursor functional group, at least one polymerizable unsaturated carbon-carbon bond, and a molecular weight of about 1,000 grams per mole or less. Materials suitable for preparing the pre-treated dental filler of the present invention include a wide variety of acid-reactive fillers, such as fluoroaluminosilicate (FAS) glass fillers. These FAS glasses are well known in the art, and include glasses such as those described in U.S. Pat. Nos. 3,655,605; 3,814, 717; 4,043,327; 4,143,018; 4,209,434 and 5,063,257. The FAS glass may contain sufficient leachable fluoride to provide useful cariostatic protection when a cement made from the glass is placed in the mouth. The FAS glass may be sufficiently finely divided to provide easy mixing, rapid cure and good handling properties in dental applications. Any convenient pulverizing or comminuting means can be employed to produce finely-divided glass. Ball-milling is a convenient approach.

In addition to FAS glass fillers, other acid-reactive fillers can also be used, including metallic oxides and hydroxides, such as zinc oxide, calcium oxide and calcium hydroxide. Acid-reactive fillers, as disclosed in U.S. Pat. No. 7,090,722, are also suitable.

Typical formulations of FAS glass ionomers include:

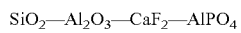

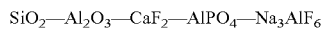

In one embodiment, an FAS glass may be prepared from a mixture of alumina, silica aluminum fluoride and calcium fluoride and optionally aluminum phosphate and cryolite (sodium aluminum fluoride). The amount of fluoride in this glass may range from about 5% to about 60%, by molar percentage.

These glasses are generally known as alkaline earth metal fluoroaluminosilicate glasses. At least a part of the alkaline earth metal may be replaced by lanthanide metals, such as lanthanum, gadolinium or ytterbium. A part or all of the alumina in these glasses may be replaced by an oxide of a Group III metal other than aluminum. Likewise, a part of the silica in these glasses may be replaced by zirconium oxide or titanium oxide. If these glasses include strontium, lanthanum, gadolinium, ytterbium or zirconium, they achieve radiopacity. It is useful to have at least about 10 wt % of a radiopaque element contained in the glass ionomer filler of the present invention.

The particle size of the acid-reactive fillers suitable for pretreatment may vary. For example, nanometer-sized fluoroaluminosilicate particles, such as those described in U.S. Pat. No. 7,361,216 are suitable for use, as well as the conventional larger glass ionomer particles ranging from about 0.2 μm to about 40 μm.

The pre-treatment chemical includes aliphatic or aromatic polymerizable resin monomers or oligomers. These polymerizable monomers or oligomers comprise at least one acid or acid-precursor functional group, such as a carboxylic acid, carboxylic acid anhydride, acyl halide, sulfonic acid, sulfonyl halide, sulfonic anhydride, sulfinic acid, sulfinyl halide, sulfinic anhydride, phosphoric acid, phosphoric acid derivative, phosphonic acid, and phosphonic acid derivative, and combinations thereof. The salts of the corresponding acid may also be used. Exemplary salts include the alkali metal salts. Additionally, the polymerizable monomers or oligomers comprise at least one polymerizable unsaturated carbon-carbon bond, such as an alkene or alkyne functional group. In one embodiment, the pre-treatment chemical is an ethylenically unsaturated acid.

In one embodiment, at least two acid or acid-precursor functional groups are present in the pre-treatment chemical. In another embodiment, the ratio between the number of acid or acid-precursor functional groups and the number of polymerizable unsaturated carbon-carbon bonds in the pretreatment chemical is between about 1:3 to about 3:1, for example, about 1:2 to about 2:1.

A pretreatment chemical having an excessively large molecular weight may cause gelation of the reaction mixture to precede the surface reaction between the acid-reactive filler and the pretreatment chemical during mixing. Thus, to avoid this detrimental effect during the pre-treatment process, the molecular weight of the pretreatment chemical should be minimized. A suitable molecular weight range of the polymerizable resin monomers or oligomers is about 1,000 grams per mole or less, for example, about 800 grams per mole or less, and by further example, about 700 grams per mole or less. In one embodiment, the range of the molecular weight is about 50 to about 800 grams per mole. In another, the molecular weight range is about 100 to about 700 grams per mole.

Exemplary pre-treatment chemicals include, but are not limited to, acrylic acid, methacrylic acid, 2-(methacryloyloxy)ethyl phosphate, bis(2-(methacryloyloxy)ethyl) phosphate, biphenyl dimethacrylate, ethylene glycol methacrylate phosphate, 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, or adduct reaction product of benzenetetracarboxylic acid di-anhydride with 2-(6-hydroxy-1-oxo-hexyloxy)ethyl methacrylate.

Another suitable class of pre-treatment chemicals is an ethylenically unsaturated phosphoric acid ester having the general formula:

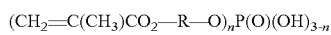

wherein R is a substituted or un-substituted alkyl or aryl group having about 1 to about 36 carbon atoms and n equals 1 or 2.

The amount of the pre-treatment chemical used for treating the acid-reactive filler may range from greater than zero to about 25 percent, based on the weight of the acid-reactive filler. For example, the amount of the pre-treatment chemical may range from about 1 to about 25 percent, and by way of further example, from about 2 to about 20 percent. Another exemplary range is from about 2 to about 15 percent. Of course, the amount of the pre-treatment chemical required to treat the acid-reactive filler may also be determined or affected by the particle sizes and the nature of the surface porosity of the acid-reactive fillers. The amount of pretreatment chemical should be sufficient to render the acid-reactive filler measurably less reactive toward acids or acid-precursors. If the pre-treated dental filler is used for a one-component dental resin restorative composition, it is favorable to use a sufficient quantity of pre-treatment chemical to render the filler essentially inactive toward acid or acid-precursors in the presence of water over a commercially reasonable storage period.

In accordance with the invention, it is generally understood that the pre-treated dental filler is produced by causing an acid or acid-precursor functional group of the pre-treatment chemical to react with the surface of the acid-reactive filler in the presence of a suitable quantity of water. The resulting reaction product is subsequently dried and pulverized to the desired particle size. Generally, the reaction is carried out in the presence of an excess amount of water. The mixing ratio of water/(filler and pre-treatment chemical) is about 0.1 to about 10 (w/w), for example the range may be from about 0.2 to about 7.5 (w/w). A deficient amount of water should be avoided because gelation may precede the desired reaction.

The process of reacting the acid with the acid-reactive filler may be carried out in a conventional reactor, or in such a reactor as an autoclave that is capable of being pressurized or heated up. The reaction is preferably carried out within a temperature range of from about room temperature to about 100° C. Under inert conditions, however, the temperature may be raised up to about 150° C.

Reaction time may be determined on the basis of the quantity of acid groups in the reaction system, though it may sometimes extend over a period of several hours to several days. Reaction between the acid and the acid-reactive filler is preferably carried out in such a manner that the content of the reactor is in an agitatable state at the beginning of reaction and is in a loose gel form state, e.g., in a yogurt-like or gruel-like condition, when the process of reaction is nearly completed.

The pre-treated dental filler of this invention may be prepared in various manners. The following three exemplary methods are useful.

The first method is a method that is conventionally employed for the production of glass ionomer cements, which comprises causing the acid-reactive glass and the pre-treatment chemical to react with each other in the presence of water, and dehydrating and drying the resulting product. The mixing ratio of the acid-reactive filler to the pre-treatment chemical may be arranged as earlier described. The mixing ratio of water/(filler and pre-treatment chemical) may range from about 0.1 to about 10 (w/w). For example, the range may be from about 0.2 to about 1.5 (w/w). The resulting material is first roughly ground to such a size as will afford ease of handling, and then ground to a desired particle size.

The second method is a powder dispersion method. This method comprises pulverizing the acid-reactive filler to a suitable particle size, and dispersing the same into the pre-treatment chemical in the presence of excess water and/or a solvent. The particle size of the glass may be about 0.1 to about 10 μm. The mixing ratio of the acid-reactive filler to the pretreatment chemical may be arranged as earlier described. To facilitate dispersion of the acid-reactive filler into the pretreatment chemical, using water in excess is favorable. The mixing ratio of water/(filler and pre-treatment chemical) may range from about 0.1 to about 10 (w/w). For example, the range may be from about 1.0 to about 7.5 (w/w). The progress of reaction between the acid-reactive filler and the pre-treatment chemical can be monitored by measuring changes in pH. After the process of reaction is nearly completed, water and/or solvent are removed. Finally, drying is effected to give a pretreated acid-reactive filter of the invention. Drying may be carried out by using any known method, e.g., simply pouring into a pan/tray in thin layer dried at room temperature or in a convection oven, by spray drying and/or freeze drying. In the event that agglomeration should occur, further pulverization may be needed. If some unreacted filler remains, the above described process may be repeated.

The third method is a simultaneous reaction and pulverization method which comprises pulverizing a melt of the acid-reactive filler in the presence of the pre-treatment chemical and excess water, while allowing a reaction to be effected in the mean time. For this purpose, balls, rods, beads, and a planetary or oscillating mill may be used. Any wet milling process may be employed. In this third method, glass agglomerates or melts of from about 3 mm to about 20 mm in bulk size are pulverized by means of a suitable mill in conjunction with acid and excess water. The pre-treatment chemical reacts with the surface of the acid-reactive filler material and, as a cement is formed on the surface, destruction occurs to allow appearance of a new reactive surfaces. Conceivably, such newly exposed surfaces may proceed to react with the pre-treatment chemical. The desired result is the production of a dispersion liquid containing fine particles of pre-treated acid-reactive filler. The mixing ratio of the acid-reactive filler to the pre-treatment chemical may be arranged as earlier described. The mixing ratio of water/(filler and pre-treatment chemical) is about 0.1 to about 10 (w/w), for example about 1.0 to about 7.5 (w/w). After the process of reaction is nearly completed, water is removed and the filler is subjected to spray drying and/or freeze drying, whereby a pre-treated acid-reactive filler of the invention is obtained.

The amount of the pre-treated acid-reactive filler in a dental composition may vary from as low as about 1 percent to as high as about 95 percent by weight, depending on the application. Exemplary applications include use as a sealant, an adhesive, a cement, a flowable composite, or a highly filled tooth restorative material. In some embodiments, the range may vary from about 5 to about 85 percent by weight. In another embodiment, the range may vary from about 10 to about 75 percent by weight. Of course, using other fillers, such as regular or treated non-reactive dental fillers as are commonly known in the art, in conjunction with the pre-treated dental fillers may be utilized to optimize the properties of the dental compositions.

The described pre-treated acid-reactive fillers are not limited only for use in the self-adhesive resin compositions as a self-adhesive cement, dental adhesive, pit and fissure sealant, core build-up material, tooth filling material or compositions for other dental applications. They can be used in regular non-acid containing polymerizable dental resin compositions to supply fluoride ion release, as well. For example, treating FAS glass with pretreatment chemicals, such as ethylenically unsaturated acids, may significantly increase the fluoride-releasing property of the glass, as shown in Example 1 and Table 1.

Moreover, while the pre-treated acid-reactive fillers are ideally suited for use in single-component dental composite compositions, their use is not limited thereto. For example, these pre-treated fillers also may be use in dual or multiple component dental composite compositions.

A dental resin restorative composition may be prepared by combining a pre-treated acid-reactive filler with a polymerizable resin and a polymerization initiator. Light-curable dental restorative composites are generally preferred and may be formed wherein the polymerization initiator is a photoinitiator. Additionally, the dental resin restorative compositions may also comprise other additives and solvents known in the art.

The composition comprises a polymerizable component, i.e., at least one polymerizable monomer or prepolymer selected from those known in the art of dental materials, including but not being limited to, resins having (1) free radically-active functional groups, (2) ionically-active functional groups, or (3) both free radically- and ionically-active functional groups.

The resin component of the dental composite composition can include a variety of resins, including free radically-polymerizable resins, ionically-polymerizable resins, or combinations thereof. Examples of free radically-polymerizable resins include, but are not limited to those resins with ethylenically unsaturated functional groups such as (meth)acrylates, vinyl monomers such as styrene, vinyl esters, a variety of unsaturated cyclic monomers such as spiro-ortho carbonates, esters, vinyl cyclic ethers and cyclic acetals. By way of further example, the pre-treatment chemicals containing acid or acid-precursor functional groups, as described above, are suitable free radically-polymerizable resins.

Examples of ionically-polymerizable resins include, but are not limited to, vinyl ethers and cyclic monomers such as epoxies, siloranes, lactides, ϵ-caprolactones and ϵ-caprolactams.

Examples of resins containing both free radically- and ionically-active functional groups include, but are not limited to the resin oligomers having both an epoxy functionality and a (meth)acrylate functionality as set forth in commonly owned U.S. Pat. No. 7,241,856, which is hereby incorporated by reference.

Preferred polymerizable monomers are ethylenically unsaturated and include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine, all of which are herein incorporated by reference in their entirety. Methacrylate-based monomers are particularly useful, including the condensation product of bisphenol A and glycidyl methacrylate; 2,2'-bis[4-(3-methacryloxy-2-hydroxy propoxy)-phenyl]-propane (BIS-GMA); dipentaerythritol pentaacrylate (DPEPA); pentaerythritol dimethacrylate (PEDM); the condensation product of ethoxylated bisphenol A and glycidyl methacrylate (EBPA-DMA); urethane dimethacrylate (UDMA); ethoxylated bisphenol A di(meth) acrylates including ethoxylated bisphenol A dimethacrylate (EBPDMA) as disclosed in U.S. Pat. No. 6,013,694 to Jia, et al.; the condensation product of 2 parts hydroxymethylmethacrylate and 1 part triethylene glycol bis(chloroformate) (PCDMA); polyurethane-based dimethacrylates (PUDMA) and polycarbonate modified-BisGMA (PCBisGMA) and other monomers set forth in commonly owned U.S. Pat. No. 6,787,629, which is hereby incorporated by reference.

The polymerizable component may further comprise additional polymerizable diluent monomers. Such monomers are generally used to adjust the viscosity of the polymerizable composition. Suitable methacrylate-based diluent monomers include, without limitation, hydroxyalkyl methacrylates, such as 2-hydroxyethyl methacrylate, 1,6-hexanediol dimethacrylate, and 2-hydroxypropyl methacrylate; glyceryl dimethacrylate; and ethylene glycol methacrylates, including ethylene glycol methacrylate, diethyleneglycol methacrylate, triethyleneglycol methacrylate and tetraethyleneglycol methacrylate. Triethyleneglycol dimethacrylate (TEGDMA) is exemplary.

The dental restorative composition may further include a polymerization photoinitiator system for light curing the polymeric material. The light cure system is selected from known light-activated polymerization initiators, including but not being limited to benzil, benzoin, benzoin methyl ether, DL-camphorquinone (CQ) and benzil diketones. Either UV-activated cure or visible light-activated cure (about 230 nm to about 750 nm) is acceptable. The amount of photoinitiator is selected according to the curing rate desired. A minimally catalytically effective amount is generally about 0.01% by weight of the polymeric components. Faster rates of cure are achieved with amounts of catalyst in the range from greater than about 0.01% to about 5% by weight of the polymeric component. Visible light curing systems may further comprise polymerization accelerators, which include various organic tertiary amines well known in the art. In visible light curable compositions, the tertiary amines may be acrylate derivatives such as dimethylaminoethyl methacrylate and, particularly, diethylaminoethyl methacrylate (DEAME) and aromatic tertiary amines such as ethyl dimethylamino benzoate (EDMAB) in amounts in the range from about 0.05 to about 2 weight percent, for example from about 0.1 to about 0.5 weight percent.

The dental restorative compositions may also comprise other additives and solvents known in the art, for example, ultra-violet light absorbers, anti-oxidants such as BHT, stabilizers, filters, pigments, opacifiers, handling agents/rheology modifiers, fluorescence agent and others. It is useful to employ an ultraviolet absorber in amounts ranging from about 0.05 to about 5.0 weight percent. Such UV absorbers are particularly desirable in these visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN® P by Ciba-Geigy Corporation, Ardsley, N.Y.

Fillers, such as particulate and fibers, colloidal silica, barium glasses, fibrous fillers, quartz, ceramic fillers and the like may also be incorporated into the compositions. Suitable fillers include fillers conventionally used in the dental industry capable of being covalently bonded to the resin matrix itself or to a coupling agent which is covalently bonded to both. Such fillers are described in U.S. Pat. Nos. 4,544,359 and 4,547,531, the pertinent portions of which are hereby incorporated by reference. Silane coupling agents are known, for example γ-methacryloxypropyltrimethoxy silane. Examples of suitable filling materials include but are not limited to amorphous silica; spherical silica; colloidal silica; barium glasses; quartz; ceramic fillers; silicate glass; hydroxyapatite; calcium carbonate; fluoroaluminosilicate; barium sulfate; quartz; barium silicate; strontium silicate; barium borosilicate; barium boroaluminosilicate; strontium borosilicate; strontium boroaluminosilicate; glass fibers; lithium silicate; ammoniated calcium phosphate; deammoniated calcium phosphate; alumina; zirconia; tin oxide; polymer powders such as, polymethyl methacrylate, polystyrene, and polyvinyl chloride; titanium dioxide; bound and nanostructured silica fillers as set forth in commonly owned U.S. Pat. No. 6,417,246, which is hereby incorporated by reference; densified and embrittled glass fibers or particles as set forth in commonly owned U.S. Pat. Nos. 6,013,694 and 6,403,676, which are hereby incorporated by reference; fibrous material and one or more forms of surface-modifying particles bonded thereto as set forth in commonly owned U.S. Pat. No. 6,270,562, which is hereby incorporated by reference; polyhedral oligomeric silsesquioxane fillers as set forth in U.S. Pat. No. 6,653,365, which is hereby incorporated by reference, and combinations of all the fillers mentioned. Particularly suitable fillers for dental filling-type materials prepared are those having a particle size in the range from about 0.1 to about 5.0 μm, together with a silicate colloid having particle sizes in the range from about 0.001 to about 0.07 μm.

This invention is illustrated by the following examples that are merely for the purpose of illustration and are not to be regarded as limiting the scope of the invention or the manner in which it can be practiced.

EXAMPLES

Materials used for the following examples are set forth in Table A below.

TABLE A

| Abbrev. | Chemical Name | Source |
| --- | --- | --- |
| 4-META | 4-Methacryloyloxyethyltrimellitic anhydride | Polyscience, PA |
| 4-MET | 4-Methacryloyloxyethyltrimellitic acid | Prepared from 4-META |
| HEMA | 2-Hydroxyethyl methacrylate | Evonik Rohm Gehm, NJ |
| BGI | IG-90-2687 - Barium glass ionomer powder | Industrial Corp., Lionville, PA |
| Schott 018090 | SrO & ZnO modified glass ionomer powder | Schott Elect. Pkg. GmbH, Germany |
| B467 | barium-boro-silicate, silane-treated | Pentron |
| PAA | Polyacrylic acid, avg MW 3,000 | Aldrich |

Example 1

Fluoride Ion Releasing Test of Glass Ionomer Powder

Pre-treatment with 4-MET Aqueous Solution: A resin mix of 4-META and a HEMA monomer was prepared in the ratio of 3:1 by weight. Variable amounts of the resin mix were added to 200 grams of distilled water that contained 4 grams of a BGI powder IG-90-2687, which had about 4 μm average particle size. The amounts of resin added were 0, 3, 6, 10, 25 and 50 weight percent, based on the weight of the BGI powder. Bach reaction mixture was stirred with a magnetic stirrer. The fluoride ion content was measured at different time periods using 15 ml of a filtered, clear solution obtained from the reaction mixture. Measurements were taken with an Accument pH Meter 25 (Fisher Scientific, NJ) and an Orion Combination Fluoride Electrode, Model 96-09 (Orion Research Inc., MA). The procedure of the free fluoride ion measurement, sample preparation and standard solutions followed the instruction manual of the Orion electrode (Orion Research Inc. Part No. 502700-031). The pH value of each solution was also monitored with an Orion pH electrode. Test results showing the pH and fluoride ion concentration of the filtered solution on days 1, 4 and 7 are summarized in Table 1:

TABLE 1

| Ratio 1[a] | Ratio 2[b] | pH (1)[c] | F$^-$ (1)[d] | pH (4) | F$^-$ (4)[d] | pH (7) | F$^-$ (7)[d] |
|---|---|---|---|---|---|---|---|
| 0 | 0 | 5.96 | 1800 | 6.54 | 1800 | 6.58 | 1900 |
| 3 | 2.25 | 5.96 | 2900 | 6.22 | 4000 | 6.22 | 3900 |
| 6 | 4.5 | 5.90 | 3400 | 6.02 | 4600 | 6.06 | 4500 |
| 10 | 7.5 | 5.68 | 3400 | 5.79 | 3600 | 5.66 | 3800 |
| 25 | 18.75 | 5.39 | 2300 | 5.52 | 2300 | 5.49 | 2100 |
| 50 | 37.5 | 4.87 | 1100 | 5.04 | 1400 | — | — |

[a]Ratio 1 is 4-MET/HEMA to BGI (% wt)
[b]Ratio 2 is 4-MET to BGI ratio (% wt)
[c]The number of days after mixture preparation is shown in parentheses.
[d]In parts per million Example 2

Surface Pre-Treated Glass Ionomer Filler Preparation

4-MET solutions were prepared by hydrolyzing 4-META in distilled water. The molar ratio of 4-META to water was varied, as listed in Table 2. Ethanol was added to dilute the mixture up to 50 ml to form a solution. Then, 25 grams of Schott 018090, with an average particle size of about 0.7 μm, was added to the ethanol solution of 4-MET to form a slurry mixture, which was stirred for 15 minutes while covered to disperse the filler. The slurries were poured into 500 ml beakers and placed in a 70° C. oven overnight to remove the solvent. The solidified pre-treated fillers were broken up and the large agglomerations were ground with a mortar and pestle. The filler identifications and 4-MET content in the fillers are presented in Table 2 below.

TABLE 2

| Sample | Ratio[a] | 4-META[b] | Water[c] | Wt %[d] |
|---|---|---|---|---|
| 1 | 1:72 | 0.5 | 2.2 | 1.9 |
| 2 | 1:36 | 1.0 | 2.2 | 3.8 |
| 3 | 1:1 | 3.05 | 0.18 | 11.3 |
| 4 | 1:4 | 3.05 | 0.8 | 11.3 |
| 5 | 1:16 | 1.52 | 0.8 | 5.6 |
| Control | N/A | 0 | 0 | 0 |

[a]4-META/H$_2$O molar ratio
[b]in grams
[c]distilled water in grams
[d]Weight percent of 4-META in dried filler sample Example 3

Fluoride Ion Release from Resin Compositions Containing 4-META

The fluoride ion (F$^-$) release enhancement was evaluated on the following compositions. Eight composites of a self adhesive resin composition, according to Example 19 of U.S. Patent Publication No. 20080242761, were prepared for comparison. Five samples respectively comprised the pre-treated filler Nos. 1 through 5 from Table 2. The three control samples were prepared using an alternate filler, respectively a non-fluoride containing regular barium-boro-silicate glass filler (Pentron filler code B467, a silane treated Schott 8235, 1.2 μm average sized filler), a regular silane-treated GI filler and a non-pre-treated BGI filler. The eight composite compositions were made by blending six grams of the self-adhesive resin composition with four grams of the respective filler to form a flowable composite material, which was packed into a dental syringe and dispensed through a 19 gauge needle tip. After removing the porosities from the paste by vacuum, composite discs of 15 mm in diameter and about 1 mm in thickness were made by injecting the materials into a metal ring (mold) between two glass slides. The materials were cured with visible light by using a Sculpture Curing Light (Pentron Laboratory Technologies, LLC, CT) for 5 minutes. Duplicated samples for each composite were prepared and tested for F$^-$ release. Each composite disc was placed in 15 ml distilled water with a covered container and aged at 37° C. for one week before the solution is obtained for F$^-$ analysis. Fresh water was added again for a second week F$^-$ measurement. The procedure of the free fluoride ion measurement, sample preparation, standard solutions and uses, etc. for the solutions collected follows the instruction manual of the Orion electrode (Orion Research Inc. Part No. 502700-031). The free fluoride ion in the solutions was measured and recorded. The average accumulated fluoride ion in ppm for each material, calculated based on the mass of the composite material unit of per gram, is presented in Table 3.

Example 4

Vicker's Hardness and DTS Test

Six cylinders (6 mm×3 mm) for each material from Example 3 were made by filling the material into a diametral tensile strength (DTS) sample mold between two glass slides and light-curing the material with a Demetron 501 light (Kerr Corporation, Orange, Calif.) for 30 seconds on the top. The samples were removed from the mold after hardening and placed in water at 37° C. for 24 hours before testing. Two of the six DTS samples were picked randomly from each testing material for the Vicker's Hardness test with a CLARK Vicker's Hardness Tester, Model MHT1 (Clark Instrument, Inc.) and then all six samples were analyzed for the DTS compression test. The descriptions of the DTS test is well known and can be found in "Restorative dental materials", pp 68-69; $9^{th}$ addition, edited by Craig, Mosby-year Book, Inc. For the Vicker's Hardness test, five readings from the top surface of each of the two selected samples were taken and the ten numbers for each material were averaged and presented in Table 3 along with the standard deviations. For the DTS test, the load at which the sample broke was recorded and calculated according to the sample parameters and DTS testing method. The testing results of the six samples for each material group were averaged and a standard deviation was calculated. The results are listed in Table 3.

TABLE 3

| 6 g of Resin[a] + 4 g of: | Average F- @ 1 week (ppm) | Total F- @ 2 weeks (ppm) | Vicker's Hardness[f,g] | DTS[g] |
|---|---|---|---|---|
| B467 filler[b,c] | — | — | 38.8 (3.4) | 44.5 (6.4) |
| Pre-treated GI #1 | 73.4 | 105.3 | 40.4 (3.4) | 36.3 (3.2) |
| Pre-treated GI #2 | 63.9 | 91.6 | 39.2 (3.1) | 38.0 (5.0) |
| Pre-treated GI #3 | 35.1 | 48.9 | 35.5 (5.1) | 33.4 (4.1) |
| Pre-treated GI #4 | 26.6 | 55.8 | 29.4 (2.6) | 31.5 (5.2) |
| Pre-treated GI #5 | 39.5 | Not measured | 37.7 (3.8) | 35.9 (3.5) |
| Schott 018090[d,e] | 11.8 | 30.9 | 32.2 (5.2) | 31.1 (4.4) |
| Schott 018090[c,d] | 18.0 | Not measured | 41.0 (5.2) | 37.1 (2.6) |

[a]Self adhesive resin composition: Example 19 of U.S. Patent Publication No. 20080242761.
[b]Non-fluoride-containing silane-treated barium glass filler
[c]Silane treated with A-174 (γ-methacryloyloxypropyltrimethoxysilane). Silane content is about 2% by weight.
[d]Fluoride-containing; Average particle size of 0.7 μm.
[e]Untreated filler
[f]After 24 hours in water
[g]MPa (Standard Deviation)

From the results above, the pre-treated glass ionomer fillers that were pre-treated with a polymerizable acid-containing monomer in the range of about 1-25% by weight in accordance with the invention have more fluoride ion releasing ability than the same glass ionomer fillers that were either not pre-treated or pretreated with a silane. Additionally, the Vicker's Hardness and DTS results show that the use of a pre-treated glass ionomer filler in dental compositions did not compromise the mechanical properties of the materials tested.

Example 5

Cure Depth and Strength of Pre-Treated Glass Ionomer Filler

The physical properties of pre-treated acid-reactive filler composites were compared. One type of pre-treated filler was obtained from pre-treatment with an ethylenically unsaturated acid, while the other type was obtained from pre-treatment with polyacrylic acid. The glass ionomer filler used for comparison was the same filler used in Example 2 of this invention, the Schott 01890 with the average particle size of 0.7 μm. The polyacrylic acid (PAA) was used as a 50% solution with an average Mw of 3,000 (commercially available from Aldrich). The PAA pre-treated glass ionomer filler was prepared in accordance with Example 20 in U.S. Pat. No. 5,883,153. The ratio of the net polyacrylic acid and water to the glass filler was calculated and used per Example 20 of U.S. Pat. No. 5,883,153. Specifically, for 30 grams of the Schott 01890 filler, 38.4 grams of the 50% polyacrylic acid solution and 359.8 ml of distilled water were used for the reaction. The filler obtained from this process is referred to as PAA-GI filler.

Four composite compositions were prepared based on components in parts per hundred, as listed in Table 4, utilizing the 4-META pre-reacted glass ionomer filler of Sample 2 in Example 2, Table 2 above. The PAA-GI filler was used for an identical formulation as a control. The Compressive and Flexural strengths were tested in accordance with ISO 9917-2 "Dental water-based cements—Part 2: Light-activated cements" and ISO 4049 "Dentistry—Polymer-based filling, restorative and luting materials", respectively (n=6). In addition, the depth of cure of the composite compositions was measured using a 3 mm×12 mm splitable, Teflon cylinder mold and the composites were cured in the mold between two glass slides from the top for 20 seconds using an Avante™ halogen curing light (Pentron). Ten minutes after the completion of the light irradiation, the specimens were removed from the mold. The height of the cylinder of cured material was measured with a micrometer to an accuracy of ±0.1 mm. The test results are listed in Table 4 below.

TABLE 4

| Components | Composite 1 | Composite 2 | Composite 3 | Composite 4 |
|---|---|---|---|---|
| A | 39 | 25.5 | 39 | 25.5 |
| B | 0.0004 | | 0.0004 | |
| C | 26 | 53.3 | 26 | 53.3 |
| D | 35 | 21.2 | | |
| E | | | 35 | 21.5 |
| Compressive strength[F] | 173.8 (51.4) | 244 (24) | 150.1 (39.1) | 204 (44.6) |
| Flexural strength[F] | 73.5 (5.9) | 87.1 (4.5) | 55.3 (5.5) | 73.6 (5.6) |
| Depth of Cure | 8.7 mm | 9.8 mm | 4.4 mm | 6.5 mm |
| Comments | G | H | G | H |

A. Polymerizable resin mix of a self-adhesive resin (Example 19 of U.S. Patent Publication No. 20080242761)
B. Blue pigment (Lake Blue #1)
C. Silane-treated Schott 8235 regular barium glass filler, 1.2 μm average particle size
D. 4-META pre-reacted glass ionomer filler (Sample #2 of Table 2)
E. PAA-GI filler (Control group)
[F]Measurement in MPa (Standard Deviation)
G. The composite material is blue tinted and has a soft and flowable consistency.
H. The composite material is while (untinted) and has a consistency of putty and full of body.

As can be seen from the results, the mechanical properties of the composite compositions using the inventive pre-treated glass ionomer fillers are stronger than the identical compositions using the preformed glass ionomer filler as disclosed in U.S. Pat. No. 5,883,153. An additional unexpected result was the increased cure depth of the composite compositions containing the inventive pre-treated glass ionomer filler, as compared to the counterparts using the preformed glass ionomer filler as taught in U.S. Pat. No. 5,883,153.

While the present invention has been illustrated by the description of one or more embodiments thereof and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. A pre-treated dental filler comprising a reaction product of an acid-reactive filler and a pre-treatment chemical, wherein the pre-treatment chemical is a polymerizable monomer or oligomer comprising:
  at least one acid group selected from the group consisting of a carboxylic acid, a sulfonic acid, a sulfinic acid, a phosphoric acid, and a phosphonic acid, or at least one acid-precursor functional group selected from the group consisting of a carboxylic acid anhydride, an acyl halide, a sulfonic anhydride, a sulfonyl halide, a sulfinic anhydride, a sulfinyl halide, a phosphoric acid derivative, and a phosphonic acid derivative;
  at least one polymerizable unsaturated carbon-carbon bond; and
  a molecular weight of about 1,000 grams per mole or less, with the proviso that where the at least one acid group is the carboxylic acid or the at least one acid-precursor functional group is the carboxylic acid anhydride, the pre-treatment chemical is selected from the group consisting of biphenyl dimethacrylate, 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, and adduct reaction product of benzenetetracarboxylic acid di-anhydride with 2-(6-hydroxy-1-oxo-hexyloxy)ethyl methacrylate, and with the proviso that where the at least one acid group is the phosphoric acid, the pre-treatment chemical is an ethylenically unsaturated phosphoric acid ester having the general formula: $(CH_2\!=\!C(CH_3)CO_2\!-\!R\!-\!O)_nP(O)(OH)_{3-n}$, wherein R is a substituted or unsubstituted alkyl or aryl group having about 1 to about 36 carbon atoms and n equals 1 or 2.

2. The pre-treated dental filler of claim 1, wherein the acid-reactive filler comprises a fluoroaluminosilicate glass.

3. The pre-treated dental filler of claim 1, wherein the molecular weight is within a range of about 50 to about 800 grams per mole.

4. The pre-treated dental filler of claim 1, wherein the molecular weight is within a range of about 100 to about 700 grams per mole.

5. The pre-treated dental filler of claim 1, wherein the acid functional group is the sulfonic acid, the sulfinic acid, or the phosphonic acid; or the acid-precursor functional group is the acyl halide, the sulfonic anhydride, the sulfonyl halide, the sulfinic anhydride, the sulfinyl halide, the phosphoric acid derivative, or the phosphonic acid derivative.

6. The pre-treated dental filler of claim 1, wherein the polymerizable monomer or oligomer has at least two acid or acid-precursor functional groups.

7. The pre-treated dental filler of claim 1, wherein a ratio between the number of acid or acid-precursor functional groups and the number of polymerizable unsaturated carbon-carbon bonds is between about 3:1 and about 1:3.

8. The pre-treated dental filler of claim 1, wherein the polymerizable monomer or oligomer comprises ethylenically unsaturated compounds.

9. The pre-treated dental filler of claim 1, wherein the pre-treatment chemical is biphenyl dimethacrylate, 4 methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, or adduct reaction product of benzenetetracarboxylic acid di-anhydride with 2-(6-hydroxy-1-oxo-hexyloxy)ethyl methacrylate.

10. The pre-treated dental filler of claim 1, wherein the pre-treatment chemical is the ethylenically unsaturated phosphoric acid ester having the general formula:

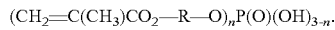

$(CH_2\!=\!C(CH_3)CO_2\!-\!R\!-\!O)_nP(O)(OH)_{3-n}.$

11. The pre-treated dental filler of claim 1, wherein the reaction product comprises greater than zero to about 25 weight percent of the pre-treatment chemical, based on the weight of the acid-reactive filler.

12. A dental restorative composition comprising:
(A) a polymerizable resin;
(B) a pre-treated dental filler comprising a reaction product of an acid-reactive filler and a pre-treatment chemical, wherein the pre-treatment chemical is a polymerizable monomer or oligomer comprising
at least one acid group selected from the group consisting of a carboxylic acid, a sulfonic acid, a sulfinic acid, a phosphoric acid, and a phosphonic acid, or at least one acid-precursor functional group selected from the group consisting of a carboxylic acid anhydride, an acyl halide, a sulfonic anhydride, a sulfonyl halide, a sulfinic anhydride, a sulfinyl halide, a phosphoric acid derivative, and a phosphonic acid derivative,
at least one polymerizable unsaturated carbon-carbon bond, and
a molecular weight of about 1,000 grams per mole or less with the proviso that where the at least one acid group is the carboxylic acid or the at least one acid-precursor functional group is the carboxylic acid anhydride, the pre-treatment chemical is selected from the group consisting of biphenyl dimethacrylate, 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, and adduct reaction product of benzenetetracarboxylic acid di-anhydride with 2-(6-hydroxy-1-oxo-hexyloxy)ethyl methacrylate, and with the proviso that where the at least one acid group is the phosphoric acid, the pre-treatment chemical is an ethylenically unsaturated phosphoric acid ester having the general formula: $(CH_2\!=\!C(CH_3)CO_2\!-\!R\!-\!O)P(O)(OH)_{3-n}$, wherein R is a substituted or unsubstituted alkyl or aryl group having about 1 to about 36 carbon atoms and n equals 1 or 2; and
(C) a polymerization initiator.

13. The dental restorative composition of claim 12, wherein the polymerization initiator is a photoinitiator.

14. The dental restorative composition of claim 12, wherein the polymerizable resin comprises an ethylenically unsaturated monomer or oligomer.

15. The dental restorative composition of claim 14, wherein the ethylenically unsaturated monomer or oligomer comprises a polyurethane dimethacrylate, a diurethane dimethacrylate, a polycarbonate dimethacrylate, an ethoxylated bisphenol A dimethacrylate, 2,2'-bis[4-(3-methacryloxy-2-hydroxypropoxy)-phenyl]propane, tri(ethylene glycol) dimethacrylate, or hexanediol dimethacrylate.

16. The dental restorative composition of claim 12, wherein the pre-treated dental filler comprises from about 1 percent to about 95 percent by weight of the total composition.

17. The dental restorative composition of claim 12, wherein the composition is a single-component dental restorative composition.

18. The dental restorative composition of claim 12 further comprising a filler material having a mean particle size of more than about 0.005 microns and less than about 70 microns.

19. The dental restorative composition of claim 18, wherein the filler material comprises a non-reactive filler.

20. The dental restorative composition of claim 19, wherein the non-reactive filler is a silane-treated filler.

21. The dental restorative composition of claim 20, wherein the silane-treated filler comprises γ-methacryloyloxypropyltrimethoxysilane-treated filler.

22. A method of making a polymerizable dental restorative composition comprising:
forming a pre-treated dental filler comprising a reaction product of an acid-reactive filler and a pre-treatment chemical, wherein the pre-treatment chemical is a polymerizable monomer or oligomer comprising
at least one acid group selected from the group consisting of a carboxylic acid, a sulfonic acid, a sulfinic acid, a phosphoric acid, and a phosphonic acid, or at least one acid-precursor functional group selected from the group consisting of a carboxylic acid anhydride, an acyl halide, a sulfonic anhydride, a sulfonyl halide, a sulfinic anhydride, a sulfinyl halide, a phosphoric acid derivative, and a phosphonic acid derivative,
at least one polymerizable unsaturated carbon-carbon bond, and
a molecular weight of about 1,000 grams per mole or less,
with the proviso that where the at least one acid group is the carboxylic acid or the at least one acid-precursor functional group is the carboxylic acid anhydride, the pre-treatment chemical is selected from the group consisting of biphenyl dimethacrylate, 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, and adduct reaction product of benzenetetracarboxylic acid di-anhydride with 2-(6-hydroxy-1-oxo-hexyloxy)ethyl methacrylate, and with the proviso that where the at least one acid group is the phosphoric acid, the pre-treatment chemical is an ethylenically unsaturated phosphoric acid ester having the general formula: $(CH_2=C(CH_3)CO_2-R-O)_nP(O)(OH)_{3-n}$, wherein R is a substituted or un-substituted alkyl or aryl group having about 1 to about 36 carbon atoms and n equals 1 or 2; and
combining the pre-treated dental filler with a polymerizable resin and a polymerization-initiator.

* * * * *

UNITED STATES PATENT AND TRADEMARK OFFICE
CERTIFICATE OF CORRECTION

PATENT NO. : 8,053,490 B2
APPLICATION NO. : 12/467448
DATED : November 8, 2011
INVENTOR(S) : Weitao Jia et al.

It is certified that error appears in the above-identified patent and that said Letters Patent is hereby corrected as shown below:

IN THE SPECIFICATIONS:

Col. 1, line 12, "teeth in, situ" should read --teeth in situ--.

Col. 5, line 51, "a new reactive surfaces." should read --a new reactive surface.--.

Col. 9, line 6, "Bach reaction mixture" should read --Each reaction mixture--.

Col. 10, line 18, "filler to forma" should read --filler to form a--.

Col. 12, line 26, "is while (untinted)" should read --is white (untinted)--.

IN THE CLAIMS:

Col. 13, lines 39-40, Claim 9, "4 meth-acryloxyethyl" should read --4–meth–acryloxyethyl--.

Col. 14, line 21, Claim 12, "$(CH_2=C(CH_3)CO_2—R—O)P(O)(OH)_{3-n}$," should read --$(CH_2=C(CH_3)CO_2—R—O)_n P(O)(OH)_{3-n}$,--.

Col. 14, line 36, Claim 15, "–phenyl]propane," should read --phenyl]-propane,--.

Signed and Sealed this
Twenty-fourth Day of January, 2012

David J. Kappos
*Director of the United States Patent and Trademark Office*